United States Patent
Peterman (10) Patent No.: US 7,678,148 B2
(45) Date of Patent: Mar. 16, 2010

(54) EXPANDABLE SPINAL IMPLANT HAVING INTERLOCKING GEOMETRY FOR STRUCTURAL SUPPORT

(75) Inventor: Marc Peterman, Memphis, TN (US)

(73) Assignee: Warsaw Orthopedic, Inc.

( * ) Notice: Subject to any disclaimer, the term of this patent is extended or adjusted under 35 U.S.C. 154(b) by 577 days.

(21) Appl. No.: 10/897,837

(22) Filed: Jul. 23, 2004

(65) Prior Publication Data
US 2006/0030943 A1  Feb. 9, 2006

(51) Int. Cl.
*A61F 2/44* (2006.01)
(52) U.S. Cl. .................................. 623/17.11
(58) Field of Classification Search ... 623/17.11–17.16; 606/61
See application file for complete search history.

(56) References Cited

U.S. PATENT DOCUMENTS

| | | | | |
|---|---|---|---|---|
| 4,759,769 A | * | 7/1988 | Hedman et al. ........... | 623/17.13 |
| 4,763,390 A | * | 8/1988 | Rooz ........................... | 24/487 |
| 4,863,476 A | | 9/1989 | Shepperd | |
| 5,059,193 A | | 10/1991 | Kuslich | |
| 5,425,773 A | * | 6/1995 | Boyd et al. ............... | 623/17.15 |
| 5,554,191 A | | 9/1996 | Lahille et al. | |
| 5,609,635 A | | 3/1997 | Michelson | |
| 5,653,763 A | | 8/1997 | Errico et al. | |
| 5,665,122 A | | 9/1997 | Kambin | |
| 5,749,916 A | | 5/1998 | Richelsoph | |
| 5,776,199 A | | 7/1998 | Michelson | |
| 5,865,848 A | | 2/1999 | Baker | |
| 5,888,228 A | | 3/1999 | Knothe et al. | |
| 5,976,187 A | | 11/1999 | Richelsoph | |
| 5,980,522 A | | 11/1999 | Koros et al. | |
| 6,019,793 A | | 2/2000 | Perren et al. | |
| 6,045,579 A | | 4/2000 | Hochshuler et al. | |
| 6,080,193 A | | 6/2000 | Hochshuler et al. | |
| 6,102,950 A | | 8/2000 | Vaccaro | |
| 6,117,174 A | * | 9/2000 | Nolan ....................... | 623/17.11 |
| 6,127,597 A | | 10/2000 | Beyar et al. | |
| 6,129,763 A | | 10/2000 | Chauvin et al. | |
| 6,143,031 A | | 11/2000 | Knothe et al. | |
| 6,159,244 A | | 12/2000 | Suddaby | |
| 6,174,334 B1 | | 1/2001 | Suddaby | |
| 6,176,882 B1 | | 1/2001 | Biedermann et al. | |
| 6,183,517 B1 | | 2/2001 | Suddaby | |

(Continued)

FOREIGN PATENT DOCUMENTS

DE     44 16 605 C1    6/1995

(Continued)

*Primary Examiner*—Pedro Philogene (57) ABSTRACT

An expandable spinal implant including at least two expandable branch portions extending generally along a longitudinal axis and each including a fixed end portion and an opposite movable end portion with the fixed end portions coupled together adjacent a base portion of the implant. A first of the branch portions includes at least one transverse projection having opposite axially-facing outer surfaces. A second of the branch portions defines at least one transverse recess having opposing axially-facing inner surfaces. The transverse projection is positioned within and displacable along the transverse recess with the outer surfaces of the projection positioned in close proximity with the inner surfaces of the recess to provide structural support to the implant subsequent to expansion. In one embodiment, the branch portions are separated from one another by at least one slot including a narrow portion that defines the close fitting transverse projection and transverse recess.

55 Claims, 5 Drawing Sheets

U.S. PATENT DOCUMENTS

| | | | |
|---|---|---|---|
| 6,190,414 B1 * | 2/2001 | Young et al. | 623/17.15 |
| 6,193,757 B1 * | 2/2001 | Foley et al. | 623/17.16 |
| 6,217,579 B1 | 4/2001 | Koros | |
| 6,332,895 B1 | 12/2001 | Suddaby | |
| 6,371,989 B1 | 4/2002 | Chauvin et al. | |
| 6,419,705 B1 | 7/2002 | Erickson | |
| 6,436,140 B1 | 8/2002 | Liu et al. | |
| 6,436,142 B1 | 8/2002 | Paes et al. | |
| 6,443,989 B1 | 9/2002 | Jackson | |
| 6,443,990 B1 | 9/2002 | Aebi et al. | |
| 6,454,806 B1 | 9/2002 | Cohen et al. | |
| 6,454,807 B1 * | 9/2002 | Jackson | 623/17.15 |
| 6,488,710 B2 | 12/2002 | Besselink | |
| 6,491,724 B1 * | 12/2002 | Ferree | 623/17.11 |
| 6,520,991 B2 | 2/2003 | Huene | |
| 6,562,074 B2 | 5/2003 | Gerbec et al. | |
| 6,576,016 B1 | 6/2003 | Hochshuler et al. | |
| 6,582,467 B1 | 6/2003 | Teitelbaum et al. | |
| 6,610,090 B1 | 8/2003 | Bohm et al. | |
| 6,962,606 B2 * | 11/2005 | Michelson | 623/17.16 |
| 7,044,971 B2 * | 5/2006 | Suddaby | 623/17.15 |
| 7,066,958 B2 * | 6/2006 | Ferree | 623/17.12 |
| 2002/0045943 A1 | 4/2002 | Uk | |
| 2002/0045945 A1 | 4/2002 | Liu et al. | |
| 2002/0072801 A1 | 6/2002 | Michelson | |
| 2002/0107574 A1 | 8/2002 | Boehm, Jr. et al. | |
| 2002/0116066 A1 | 8/2002 | Chauvin et al. | |
| 2002/0128713 A1 | 9/2002 | Ferree | |
| 2002/0143401 A1 | 10/2002 | Michelson | |
| 2002/0147496 A1 | 10/2002 | Belef et al. | |
| 2002/0151977 A1 | 10/2002 | Paes et al. | |
| 2002/0177898 A1 | 11/2002 | Crozet | |
| 2003/0004575 A1 | 1/2003 | Erickson | |
| 2003/0050701 A1 | 3/2003 | Michelson | |
| 2003/0130739 A1 | 7/2003 | Gerbec et al. | |
| 2004/0010315 A1 | 1/2004 | Song | |
| 2004/0044411 A1 | 3/2004 | Suddaby | |

FOREIGN PATENT DOCUMENTS

| | | |
|---|---|---|
| EP | 0 880 950 A1 | 12/1998 |
| EP | 0 767 636 B1 | 1/1999 |
| EP | 0 857 042 B1 | 11/2001 |
| GB | 2377 387 A | 1/2003 |
| WO | WO 97/00054 | 1/1997 |
| WO | WO 99/26562 | 6/1999 |
| WO | WO 99/38460 | 8/1999 |
| WO | WO 99/66867 | 12/1999 |
| WO | WO 00/12033 | 3/2000 |
| WO | WO 00/44319 | 8/2000 |
| WO | WO 00/49977 | 8/2000 |
| WO | WO 01/01895 A1 | 1/2001 |
| WO | WO 01/56513 A1 | 8/2001 |
| WO | WO 01/72246 A1 | 10/2001 |
| WO | WO 02/19952 A1 | 3/2002 |
| WO | WO 03/105673 A2 | 12/2003 |

* cited by examiner

EXPANDABLE SPINAL IMPLANT HAVING INTERLOCKING GEOMETRY FOR STRUCTURAL SUPPORT

FIELD OF THE INVENTION

The present invention relates generally to the field of expandable spinal implants, and more particularly relates to expandable spinal implants having interlocking geometry for structural support.

BACKGROUND

There have been numerous attempts to develop a spinal implant to replace a damaged or degenerated natural spinal disc and to maintain sufficient stability of the intervertebral disc space between adjacent vertebrae, at least until arthrodesis is achieved. These types of spinal implants have taken many forms.

For example, some spinal implants are designed to expand in such a manner as to restore and/or maintain the natural anatomic angle between the adjacent vertebrae. To accomplish this result, some implant designs include multiple branches having stationary ends that are attached or otherwise coupled together and movable ends that remain unattached so as to allow the movable ends to expand apart relative to one another to provide the implant with a select taper angle corresponding to the natural anatomic angle between the adjacent vertebrae. Expansion of the implant typically relies on axial displacement of an expansion member or wedge along tapered inner surfaces defined by the branches. One example of such an implant design is illustrated and described in U.S. Pat. No. 6,436,140 to Liu et al., the contents of which are incorporated herein by reference.

Expandable spinal implants typically rely on relatively slender or weakened structures or features that allow for material deformation of certain portions of the implant, which in turn facilitates expansion of the implant in one or more directions. However, the slender or weakened features that allow for material deformation tend to compromise the structural integrity of the implant and reduce resistance to loading, particularly resistance to buckling and shear loads exerted onto the spinal implant by the adjacent vertebrae. Accordingly, incorporation of features into the spinal implant which facilitate expansion may result in a reduction in the overall structural integrity of the implant.

Thus, there is a general need in the industry to provide an improved expandable spinal implant. The present invention satisfies this need and provides other benefits and advantages in a novel and unobvious manner.

SUMMARY

The present invention relates generally to an expandable spinal implant. While the actual nature of the invention covered herein can only be determined with reference to the claims appended hereto, certain forms of the invention that are characteristic of the preferred embodiments disclosed herein are described briefly as follows.

In one form of the present invention, an expandable spinal implant is provided which includes a body extending generally along a longitudinal axis between first and second end portions and defining at least one slot extending from the first end portion toward the second end portion to provide the body with at least two expandable branch portions coupled together adjacent the second end portion. The slot includes a narrow portion defining close fitting interlocking features between the branch portions to provide structural support to the implant subsequent to expansion.

In another form of the present invention, an expandable spinal implant is provided which includes at least two expandable branch portions extending generally along a longitudinal axis and each including a fixed end portion and an opposite movable end portion with each of the fixed end portions coupled together adjacent a fixed base portion of the implant. A first of the branch portions includes at least one transverse projection having opposite axially-facing outer surfaces, and a second of the branch portions defines at least one transverse recess having opposing axially-facing inner surfaces. The transverse projection is positioned within and displacable along the transverse recess with the outer surfaces of the projection positioned in close proximity with respective ones of the inner surfaces of the recess to provide structural support to the spinal implant subsequent to expansion.

In another form of the present invention, an expandable spinal implant is provided which includes at least two expandable branch portions extending generally along a longitudinal axis and each including a fixed end portion and an opposite movable end portion with each of the fixed end portions coupled together adjacent a fixed base portion of the implant. A first of the branch portions includes a first bone engaging surface adapted to engage an adjacent vertebra and defines at least one projection arranged transverse to said first bone engaging surface. A second of the branch portions includes a second bone engaging surface adapted to engage an adjacent vertebra and defines at least one recess arranged transverse to the second bone engaging surface. The projection is positioned within and displacable along the recess to provide structural support to the spinal implant subsequent to expansion.

In another form of the present invention, an expandable spinal implant is provided which includes at least two expandable branch portions extending generally along a longitudinal axis and coupled together to allow relative pivotal movement therebetween about a pivot axis. A first of the branch portions includes at least one projection having an outer surface extending generally along a radial arc relative to the pivot axis. A second of the branch portions defines at least one recess having an inner surface extending generally along the radial arc. The projection is positioned within and displacable along the recess with the outer surface of the projection positioned in close proximity with the inner surface of the recess to provide structural support to the spinal implant subsequent to expansion.

In another form of the present invention, an expandable spinal implant is provided which includes at least two expandable branch portions extending generally along a longitudinal axis and each including a fixed end portion and an opposite movable end portion, with each of the fixed end portions coupled together at a fixed base portion of the implant. The fixed base portion of the implant has an outer surface facing away from the branch portions and defining a concave curvature to facilitate transverse expansion of the implant.

It is one object of the present invention to provide an improved expandable spinal implant. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation on the scope of the invention is hereby intended, and that alterations and further modifications in the illustrated devices, and further applications of the principles of the invention as illustrated herein are contemplated as would normally occur to one skilled in the art to which the invention relates.

Figure 1:
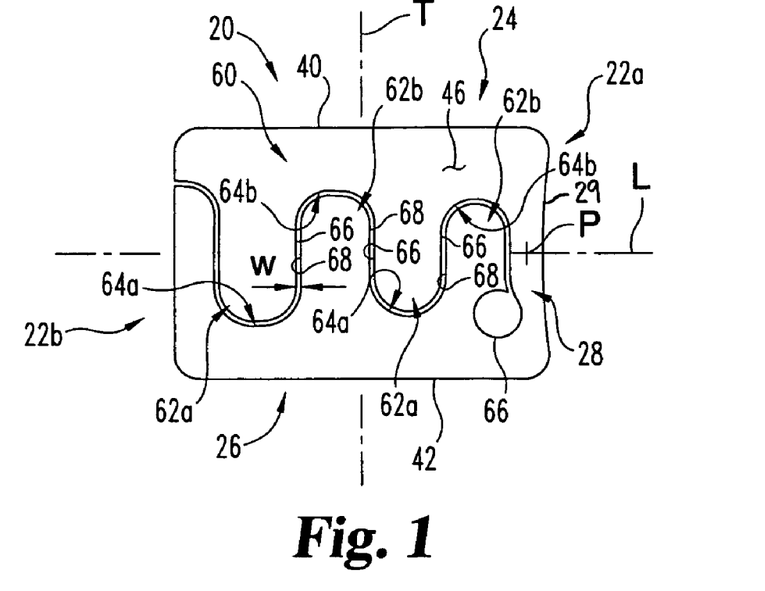
FIG. 1 is a side view of an expandable spinal implant according to one form of the present invention, as shown in a non-expanded state.

Referring to FIG. 1, illustrated therein is an expandable spinal implant 20 according to one form of the present invention. The spinal implant 20 extends along a longitudinal axis L and is configured to expand generally along a transverse axis T so as to distract an intervertebral disc space and/or to restore or maintain lordosis between the adjacent vertebrae. However, it should be understood that expansion of the spinal implant 20 may occur in multiple directions and along multiple axes. An expansion mechanism serves to transition the spinal implant 20 from the initial configuration illustrated in FIG. 1 toward the expanded configuration illustrated in FIG. 4. Further details regarding the expansion of the spinal implant 20 will be discussed below.

The spinal implant 20 is preferably formed of a biocompatible material. In one embodiment, the spinal implant 20 is formed of a medical grade alloy such as, for example, titanium. However, the use of other metallic materials are also contemplated, including stainless steel and stainless steel alloys, titanium and titanium alloys, shape-memory alloys, cobalt chrome alloys, or any combination of metallic materials. Additionally, it should be understood that forming the spinal implant 20 from a non-metallic material is also contemplated. For example, in other embodiments, the spinal implant 20 may be formed of a polymeric material, including, for example, a non-resorbable polymer such as polyetheretherketone (PEEK) or a resorbable polymer such as polylactate (PLA). In further embodiments, the spinal implant 20 may be formed of bone or bone substitute materials. Examples of other suitable materials for forming the spinal implant 20 include composite polymers, non-reinforced polymers, carbon-reinforced polymer composites, carbon fiber, PMMA, calcium hydroxide, ceramics, polylactide, polyglycolide, tyrosine-derived polycarbonate, polyanhydride, polyorthoester, polyphosphazene, calcium phosphate, calcium hydroxide, hydroxyapatite, bioactive glass, or any combination of these materials.

The spinal implant 20 includes a proximal end portion 22*a* and a distal end portion 22*b*. In one embodiment, the spinal implant 20 is generally comprised of an upper branch portion 24 and a lower branch portion 26, each extending generally along the longitudinal axis L and interconnected to one another adjacent the proximal end portion 22*a* via a fixed base portion 28. However, it should be understood that the spinal implant 20 may define any number of branch portions, including three, four, or five or more branch portions. As will be discussed below, actuation of the expansion mechanism causes the branch portions 24, 26 to separate or splay apart to provide the spinal implant 20 with a cross sectional dimension adjacent the distal end portion 22*b* that is greater than the cross sectional dimension adjacent the proximal end portion 22*a*.

In the illustrated embodiment, the branch portions 24, 26 are coupled to the fixed base portion 28 in such a manner as to allow the branch portions 24, 26 to move relative to one another to provide for expansion of the spinal implant 20. In one embodiment, expansion of the spinal implant 20 results from relative pivotal movement of the branch portions 24, 26 about a pivot axis P positioned along the fixed base portion 28 adjacent the proximal end portion 22*a*. However, other types of relative movement between the branch portions 24, 26 are also contemplated as falling within the scope of the present invention. In a further embodiment, the fixed base portion 28 is relatively thin or slender and has a predetermined configuration that provides for controlled deformation or buckling in a predetermined and repeatable fashion. In this manner, expansion of the spinal implant 20 can be correspondingly controlled via controlling the positioning of the pivot axis P and the relative orientation and positioning of the upper and lower branch portions 24, 26. In the illustrated embodiment, the fixed base portion 28 has a curved or arcuate configuration defining a concave outer surface 29 to facilitate expansion of the spinal implant 20 and to provide a degree of control over the expansion characteristics of the spinal implant 20. However, other configurations of the fixed base portion 28 are also contemplated as falling within the scope of the present invention.

In one embodiment of the invention, the branch portions 24, 26 are formed integral with the base portion 28 to define a single-piece, unitary spinal implant 20. In this manner, the base portion 28 flexibly interconnects the branch portions 24, 26 so as to allow for expansion of the spinal implant 20 via flexible material deformation of the branch portions 24, 26 and/or the fixed base portion 28. The interconnection between the fixed base portion 28 and the branch portions 24, 26 acts in a hinge-like manner during expansion of the spinal implant 20 to provide for substantially independent movement of the branch portions 24, 26. Although the illustrated embodiment of the spinal implant 20 utilizes integrally connected branch portions 24, 26, it is also contemplated that the branch portions 24, 26 may be formed separately and connected together to form a multi-piece implant assembly. In another embodiment, the branch portions 24, 26 may be pivotally attached to the base portion 28 or directly to one other via a hinge or pivot pin such that the spinal implant 20 may be expanded without relying on flexible material deformation. Other suitable means for coupling the branch portions 24, 26 together to provide for expansion of the spinal implant 20 are also contemplated, including forming or coupling of the branch portions 24, 26 directly to one another without the use of a fixed base portion 28.

Figure 3:
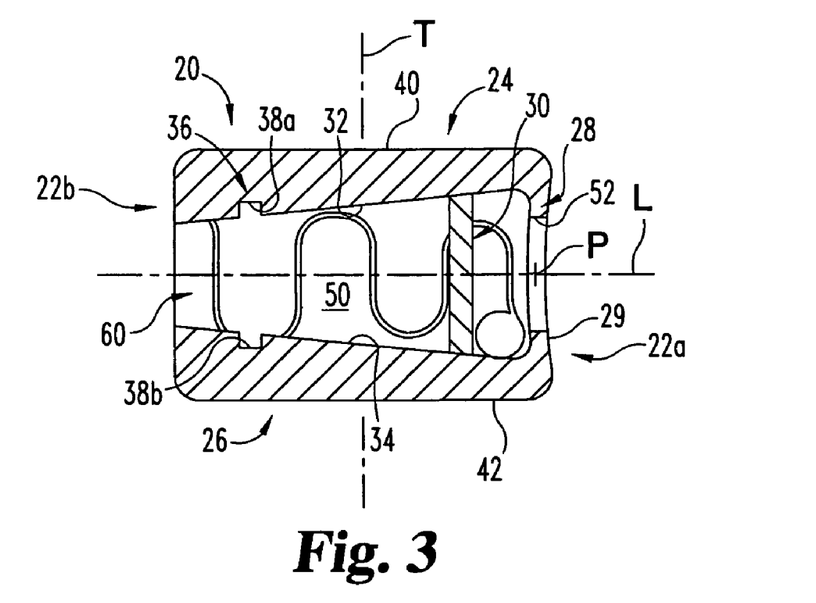
FIG. 3 is a cross-sectional view of the expandable spinal implant illustrated in FIG. 2, as taken along line 3-3 of FIG. 2.

In the illustrated embodiment of the invention, expansion of the spinal implant 20 occurs in response to axial displacement of an expansion member or wedge 30 generally along the longitudinal axis L between the branch portions 24, 26. Axial displacement of the expansion member 30 in turn causes the branch portions 24, 26 to separate or splay apart, thereby expanding the spinal implant 20 along the transverse axis T. Specifically, as illustrated in FIG. 3, the expansion member 30 is slidably displaced along opposing tapered surfaces 32, 34 defined by the branch portions 24, 26, which in turn wedges the branch portions 24, 26 apart to expand the spinal implant 20 along the transverse axis T.

In a further embodiment, the tapered surfaces 32, 34 define a retention element or interlock feature 36 adjacent the distal end portion 22b of the implant 20 which is configured to retain or lock the expansion member 30 in a select axial position relative to the spinal implant 20 and also maintains the spinal implant 20 in a select expanded configuration. In the illustrated embodiment, the retention element 36 comprises a pair of opposing notches or recesses 38a, 38b sized and shaped to receive a corresponding portion of the expansion member 30 therein. In one embodiment, the notches 38a, 38b have a box-like configuration defining opposing axially-facing surfaces that prevent axial movement of the expansion member 30 relative to the implant 20, as well as opposing laterally-facing surfaces that prevent lateral movement of the expansion member 30 relative to the implant 20. As a result, positioning of the expansion member 30 within the notches 38a, 38b also serves to resist loading exerted onto the spinal implant 20 by the adjacent vertebrae such as, for example, transverse or lateral loading and compressive loading adjacent the distal end portion 22b of the implant 20. Although the retention element 36 has been illustrated and described as comprising a pair of notches 38a, 38b, it should be understood that other types and configurations of retention elements or interlock features are also contemplated. For example, the retention element 36 may alternatively comprise ratchets, internal threads, or other suitable features configured to engage a corresponding portion of the expansion member 30.

Although expansion of the spinal implant 20 has been illustrated and described as occurring in response to axial displacement of the expansion member 30 along the branch portions 24, 26, it should be understood that in other embodiments of the invention, rotational or pivotal displacement of an expansion member 30 relative to the branch portions 24, 26 may be used to cause the spinal implant 20 to expand. Other types of relative displacement between the expansion member 30 and the branch portions 24, 26 are also contemplated for use in association with the present invention, including, for example, displacement of the expansion member 24 in directions transverse to the longitudinal axis L. In another embodiment, an instrument or tool (not shown) may be provided that is configured to engage the branch portions 24, 26 and drive the branch portions 24, 26 apart to expand the spinal implant 20 along the transverse axis T. In still another embodiment of the invention, at least a portion of the spinal implant 20 may be formed of a shape-memory material such as, for example, Nitinol, to provide the spinal implant 20 with self-expanding capabilities so as to eliminate the requirement for a separate expansion member or expansion instrument.

Figure 2:
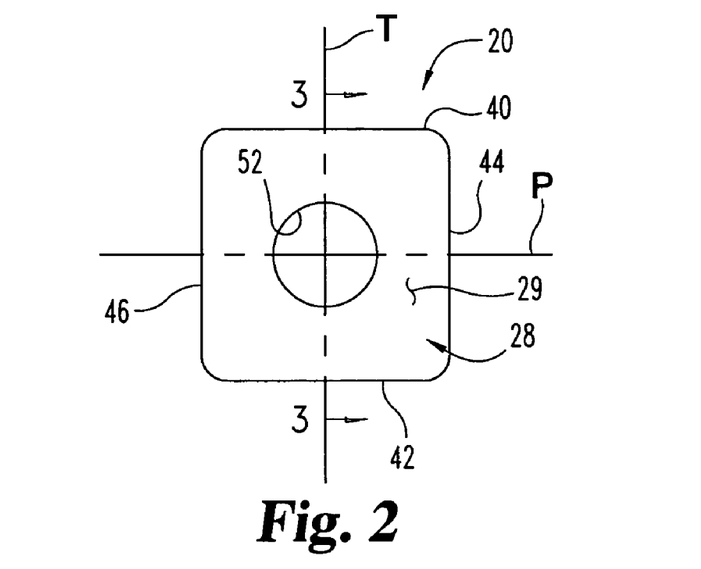
FIG. 2 is an end view of the expandable spinal implant illustrated in FIG. 1.

In the illustrated embodiment of the spinal implant 20, the branch portions 24, 26 define oppositely-disposed upper and lower bone engaging surfaces 40, 42 having a generally flat or planar configuration, and oppositely-disposed side surfaces 44, 46 extending between the bone engaging surfaces 40, 42 and also having a generally flat or planar configuration. In the illustrated embodiment, the branch portions 24, 26 cooperate with one another to define a substantially rectangular outer cross section. However, it should be understood that other shapes and configurations of the spinal implant 20 and the branch portions 24, 26 are also contemplated as falling within the scope of the present invention, including, for example, a curved or arcuate configuration, a cylindrical configuration, an elliptical configuration, a conical configuration, or any other suitable shape or configuration that would occur to one of skill in the art.

In a further embodiment of the invention, the spinal implant 20 may be configured to have a cage-like configuration, with the branch portions 24, 26 cooperating with one another to define a hollow interior or passage 50 extending generally along the longitudinal axis L. However, it should be understood that other embodiments of spinal implants 20 are also contemplated that do not define a hollow interior, but instead define a substantially solid configuration. A bone growth promoting material such as, for example, a bone morphogenetic protein (BMP) or other types of bone growth promoting materials may be positioned within the hollow interior 50 of the spinal implant 20 to facilitate fusion with the adjacent vertebrae. An opening or passage 52 may also be defined through the fixed base portion 28 to provide access to the hollow interior 50 for loading the bone growth promoting material into the hollow interior 50 and/or for receiving an end portion of an instrument or tool therethrough for engagement with the expansion member 30 to transition the spinal implant 20 to the expanded configuration.

Although not specifically illustrated in the drawing figures, in other embodiments of the invention, each of the branch portions 24, 26 may define at least one bone in-growth opening or window (not shown) extending through the bone engaging surfaces 40, 42 and/or the side surfaces 44, 46 and communicating with the hollow interior 50. As should be appreciated, the bone in-growth openings or windows permit bone growth from the adjacent vertebrae and into and possibly through the spinal implant 20. In further embodiments of the invention, the bone engaging surfaces 40, 42 may define a number of bone anchoring elements (not shown) adapted for engagement with the adjacent vertebrae to prevent or inhibit movement of the spinal implant 20 once implanted within the intervertebral disc space. In a specific embodiment, the bone anchoring elements may comprise surface irregularities extending along a substantial portion of the length of the spinal implant 20. For example, various types and configurations of surface projections may be provided including, for example, ridges, teeth, spikes, threads, surface roughening, or any other suitable bone anchoring element that would occur to one of skill in the art.

In order to facilitate expansion of the spinal implant 20 along the transverse axis T, the branches 24, 26 are separated from one another by a wire-like slot or channel 60 extending longitudinally from the distal end 22b toward the proximal end 22a and terminating adjacent the fixed base portion 28. The slot 60 extends laterally through the spinal implant 20 so as to divide the spinal implant 20 into two discrete upper and lower branch portions 24, 26. In embodiments where the spinal implant 20 defines a hollow interior 50, the spinal implant 20 defines a pair of oppositely disposed slots 60 extending from respective side surfaces 44, 46 and into communication with the hollow interior 50. However, in embodiments where the spinal implant 20 defines a substantially solid configuration, the spinal implant 20 may define a single slot extending laterally therethrough between the side surfaces 44, 46.

In one embodiment, the slots 60 terminate at an enlarged slot portion 66 adjacent the fixed base portion 28 to increase flexibility at the interconnection location between the branch portions 24, 26 and the fixed base portion 28 so as to facilitate transitioning of the spinal implant 20 to an expanded configuration, while at the same time tending to decrease stress concentrations which might otherwise develop at the interconnection location. The enlarged slot portion 66 may also be used as a means for receiving a corresponding portion of an instrument or tool to aid in the manipulation and handing of the spinal implant 20.

In the illustrated embodiment of the spinal implant 20, the slots 60 have an undulating or wavy configuration extending generally along the longitudinal axis L such that the branch portions 24, 26 define a number of projections or peaks that are disposed within a corresponding number of recesses or valleys, with the projections and recesses each extending generally along the transverse axis T. As illustrated in FIG. 1, the shape and configuration of the slots 60 provide the upper branch portion 24 with a number of projections or peaks 62a that are nested within a corresponding number of recesses or valleys 64a defined by the lower branch portion 26. Similarly, the lower branch portion 24 is provided with a number of projections or peaks 62b that are nested within a corresponding number of recesses or valleys 64b defined by the upper branch portion 24. As a result, the projections 62a, 62b are nested within the recesses 64a, 64b in an interdigitating or puzzle-like manner, the purpose of which will be discussed below.

In one specific embodiment, the width w of the slots 60 is narrow so as to provide a relatively close or congruent fit between the axially-facing surfaces 66 of the projections 62a, 62b and the axially-facing surfaces 68 of the corresponding recesses 64a, 64b. In a further embodiment, the axially-facing surfaces 66, 68 each extend generally along a radial arc relative to the pivot axis P. In this manner, adjacent axially-facing surfaces 66, 68 and adjacent projections 62a, 62b will not interfere with one another as the upper and lower branches 24, 26 are separated or splayed apart during expansion of the spinal implant 20. Although a specific configuration of the slots 60 has been illustrated and described herein, it should be understood that other suitable slot configurations are also contemplated as falling within the scope of the present invention.

Figure 4:
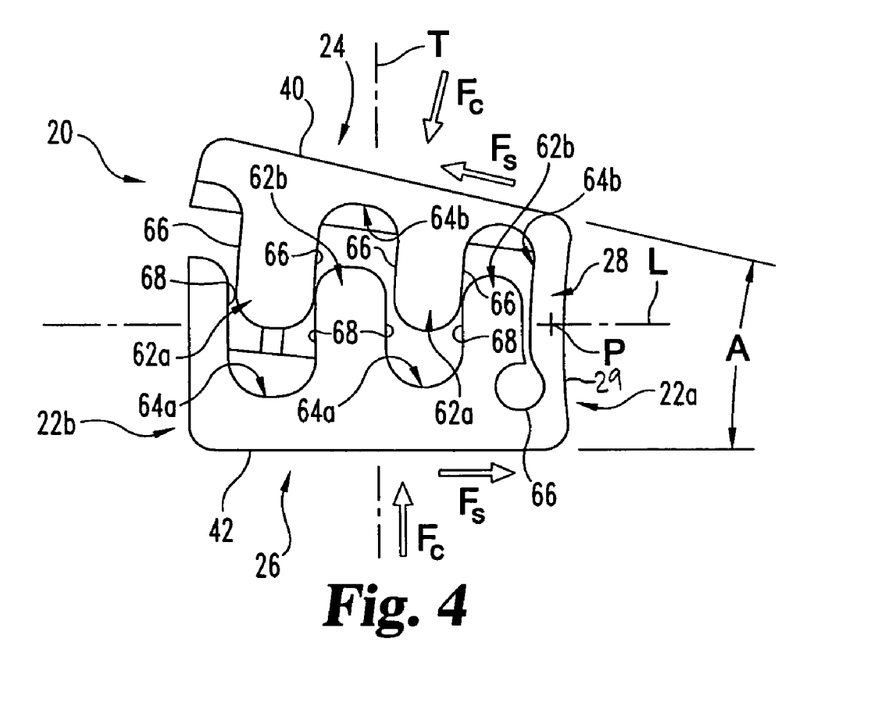
FIG. 4 is a side view of the expandable spinal implant illustrated in FIG. 1, as shown in an expanded state.

Referring to FIG. 4, illustrated therein is the spinal implant 20 show in an expanded configuration. As discussed above, the upper and lower branch portions 24, 26 are pivotally displaced away from one another relative to the pivot axis P to transition the spinal implant 20 from the initial, non-expanded configuration illustrated in FIG. 1 to the expanded configuration illustrated in FIG. 4. Additionally, during expansion of the spinal implant 20, the projections 62a, 62b are radially displaced along the recesses 64a, 64b relative to the pivot axis P. When transitioned to the expanded configuration, the bone engaging surfaces 40, 42 are angled relative to one another so as to provide the spinal implant 20 with a configuration corresponding to the particular geometry associated with the intervertebral disc space (e.g., the lordotic angle between the adjacent vertebrae). In one embodiment, the bone engaging surfaces 40, 42 define a taper angle A falling within a range of 0 degrees to about 30 degrees. In a more specific embodiment, the taper angle A is approximately 10 degrees. However, it should be understood that other taper angles A are also contemplated as falling within the scope of the present invention.

As the spinal implant 20 is transitioned to the expanded configuration, portions of the projections 62a, 62b are maintained within the corresponding recesses 64a, 64b in an interdigitating or interlocking manner to provide structural support to the expanded spinal implant 20. As should be appreciated, engagement between the axially-facing surfaces 66 of the projections 62a, 62b and the axially-facing surfaces 68 of the recesses 64a, 64b resists physiologic loading of the spinal implant 20 in the direction of the longitudinal axis L, and more particularly shear loading forces $F_S$ exerted onto the spinal implant by the adjacent vertebrae. Additionally, engagement of the projections 62a, 62b within the recesses 64a, 64b resists buckling of the relatively thin fixed base portion 28 in response to the compressive loading forces $F_C$ exerted onto the spinal implant by the adjacent vertebrae. As should be appreciated, the close congruity and interdigitating fit of the projections 62a, 62b within the recesses 64a, 64b provide structural support to the spinal implant 20 which resists physiologic shearing and bucking loading without significantly impeding or effecting the expansion characteristics of the spinal implant 20.

Figure 5:
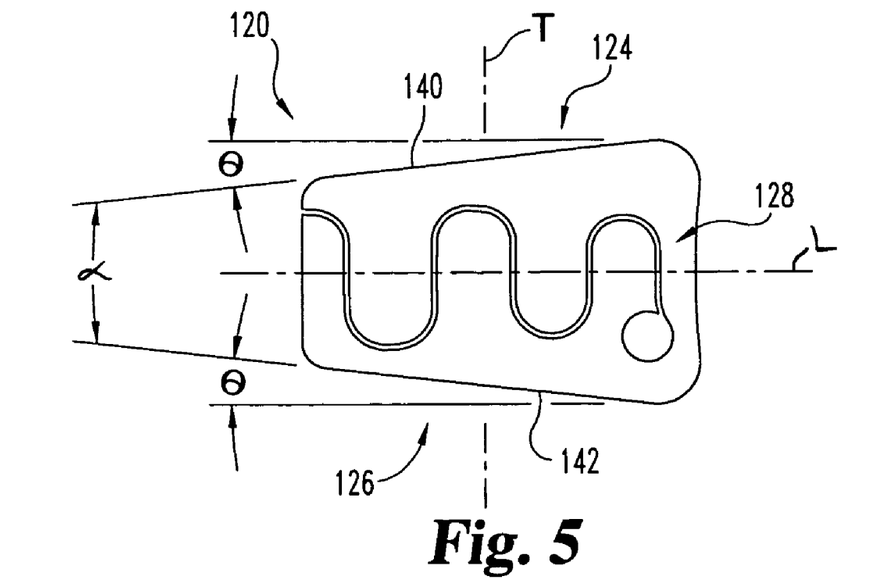
FIG. 5 is a side view of an expandable spinal implant according to another form of the present invention, as shown in a non-expanded state.
Figure 6:
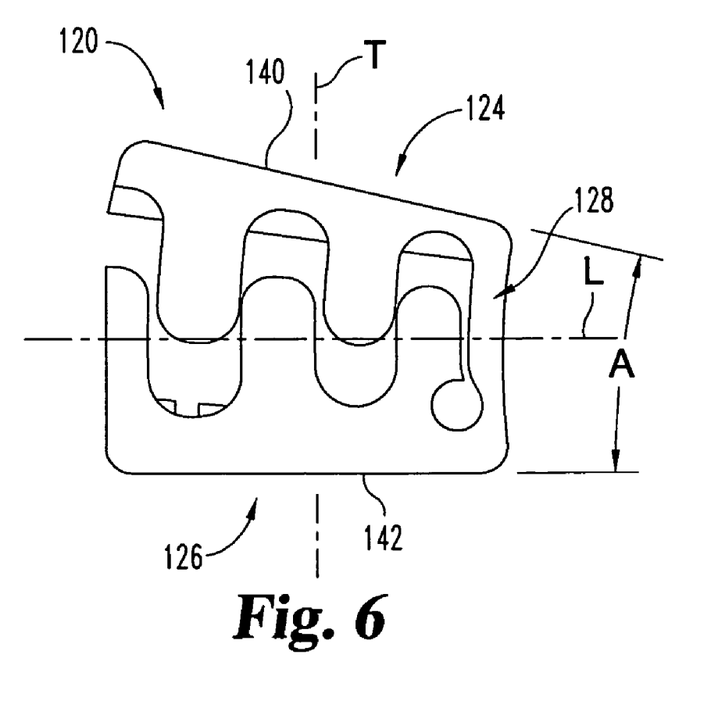
FIG. 6 is a side view of the expandable spinal implant illustrated in FIG. 5, as shown in an expanded state.

Referring to FIGS. 5 and 6, illustrated therein is an expandable spinal implant 120 according to another form of the present invention. The spinal implant 120 extends along a longitudinal axis L and is structurally similar to the spinal implant 20 illustrated and described above, including upper and lower branch portions 124, 126 interconnected by a fixed base portion 128, and with the branch portions 124, 126 defining upper and lower bone engaging surfaces 140, 142. However, unlike the bone engaging surfaces 40, 42 of the spinal implant 20 which are initially arranged generally parallel to one another when in the initial non-expanded configuration (FIG. 1), the bone engaging surfaces 140, 142 of the spinal implant 120 are angled relative to one another when in an initial non-expanded configuration (FIG. 5).

As illustrated in FIG. 5, when in the initial non-expanded configuration, the bone engaging surfaces 140, 142 of the branch portions 124, 126 are angled relative to the longitudinal axis L to provide the spinal implant 120 with a tapered configuration to facilitate insertion of the spinal implant 120 into the intervertebral disc space and/or to facilitate distraction of the adjacent vertebrae. In one embodiment, each of the bone engaging surfaces 140, 142 are tapered at an angle θ relative to the longitudinal axis L so as to provide the spinal implant 120 with an initial overall taper angle α. In one specific embodiment, the angle θ falls within a range of 0 degrees to about 15 degrees to provide the spinal implant 120 with an initial overall taper angle α of between 0 degrees to about 30 degrees. In a more specific embodiment, the angle θ is approximately 5 degrees to provide the spinal implant 120 with an initial overall taper angle α of approximately 10 degrees. However, it should be understood that other angles θ and initial overall taper angles α are also contemplated as falling within the scope of the present invention.

As illustrated in FIG. 6, when transitioned to the expanded configuration, the bone engaging surfaces 140, 142 of the branch portions 124, 126 are angled relative to one another so as to provide the spinal implant 120 with a configuration corresponding to the particular geometry associated with the intervertebral disc space (e.g., the lordotic angle between the adjacent vertebrae). Additionally, expansion of the spinal implant 120 may also serve to distract the intervertebral disc space in addition to restoring and/or maintaining lordosis between the adjacent vertebrae. In one embodiment, the bone engaging surfaces 140, 142 are tapered relative to one another so as to provide the spinal implant 120 with an expanded taper angle A. In a specific embodiment, the expanded taper angle A falls within a range of between 0 degrees to about 30 degrees. In another specific embodiment, the expanded taper angle A is approximately 10 degrees. However, it should be understood that other expanded taper angles A are also contemplated as falling within the scope of the present invention.

Figure 7:
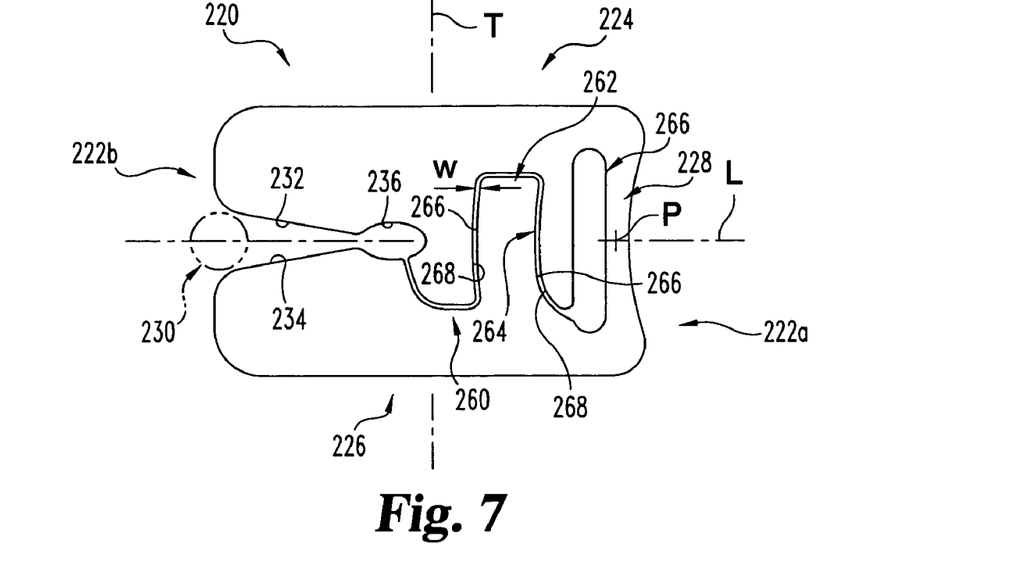
FIG. 7 is a side view of an expandable spinal implant according to another form of the present invention.

Referring to FIG. 7, illustrated therein is an expandable spinal implant 220 according to another form of the present invention. The spinal implant 220 extends along a longitudinal axis L and is structurally similar to the spinal implant 20 illustrated and described above, including a proximal end portion 222a, a distal end portion 222b, and upper and lower branch portions 224, 226 interconnected by a fixed base portion 228 in a manner which allows the branch portions 224, 226 to move relative to one another to expand the spinal implant 220 generally along a transverse axis T. In the illustrated embodiment, expansion of the spinal implant 220 results from relative pivotal movement of the branch portions 224, 226 about a pivot axis P positioned along the fixed base portion 228. However, other types of relative movement between the branch portions 224, 226 are also contemplated as falling within the scope of the present invention. In one embodiment, expansion of the spinal implant 220 occurs in response to axial displacement of an expansion member 230 (shown in phantom) along a pair of opposing tapered surfaces 232, 234 defined by the branch portions 224, 226, which in turn wedges the branch portions 224, 226 apart to expand the spinal implant 220 along the transverse axis T. Additionally, the tapered surfaces 232, 234 define a retention element or recess 236 configured to retain or lock the expansion member in a select axial position relative to the spinal implant 220 and to maintain the spinal implant 220 in a select expanded configuration.

In order to facilitate expansion of the spinal implant 220 along the transverse axis T, the branches 224, 226 are separated from one another by a wire-like slot or channel 260 extending longitudinally from the distal end 222b of the spinal implant 220 toward the proximal end 222a and terminating adjacent the fixed base portion 228. The slot 260 extends laterally through the spinal implant 220 so as to divide the spinal implant 220 into two discrete upper and lower branch portions 224, 226. In the illustrated embodiment, the slot 260 terminates at an enlarged slot portion 266 adjacent the fixed base portion 228 to increase flexibility at the interconnection location between the branch portions 224, 226 and the fixed base portion 228 to facilitate transitioning of the spinal implant 220 to an expanded configuration, while at the same time tending to decrease stress concentrations which might otherwise develop at the interconnection location. In one embodiment, the slot 260 includes a U-shaped portion that provides the branch portions 224, 226 with a projection 262 nested within a corresponding recess 264, with the projection 262 and recess 264 extending generally along the transverse axis T. In the illustrated embodiment, the shape and configuration of the slot 260 provides the upper branch portion 224 with the recess 264 and the lower branch portion 226 with the projection 262, however, a reverse configuration is also contemplated. The projection 262 is nested within the recess 264 in an interdigitating or puzzle-like manner.

In one embodiment, the width w of the slot 260 is narrow so as to provide a relatively close or congruent fit between the axially-facing surfaces 266 of the projection 262 and the axially-facing surfaces 268 of the recess 264. In a further embodiment, the axially-facing surfaces 266, 268 each extend generally along a radial arc relative to the pivot axis P. In this manner, the opposing axially-facing surfaces 266, 268 will not interfere with one another as the upper and lower branches 224, 226 are separated or splayed apart during expansion of the spinal implant 220. Although a specific configuration of the slots 260 has been illustrated and described herein, it should be understood that other suitable slot configurations are also contemplated as falling within the scope of the present invention.

As should be appreciated, during expansion of the spinal implant 220, the projection 262 is radially displaced along the recess 264 relative to the pivot axis P. As the spinal implant 220 is transitioned to the expanded configuration, a portion of the projection 262 is maintained within the recess 264 in an interdigitating or interlocking manner to provide structural support to the expanded spinal implant 220. Engagement between the axially-facing surfaces 266 of the projection 262 and the axially-facing surfaces 268 of the recess 264 resists physiologic loading of the spinal implant 220 in the direction of the longitudinal axis L, and more particularly shear loading forces exerted onto the spinal implant by the adjacent vertebrae. Additionally, engagement of the projection 262 within the recess 264 resists buckling of the relatively thin fixed base portion 228 in response to the compressive loading forces exerted onto the spinal implant by the adjacent vertebrae. Moreover, the close congruity and interdigitating fit of the projection 262 within the recess 264 provide structural support to the spinal implant 220 which resists physiologic shear and bucking loading without significantly impeding or effecting the expansion characteristics of the spinal implant 220.

Figure 8:
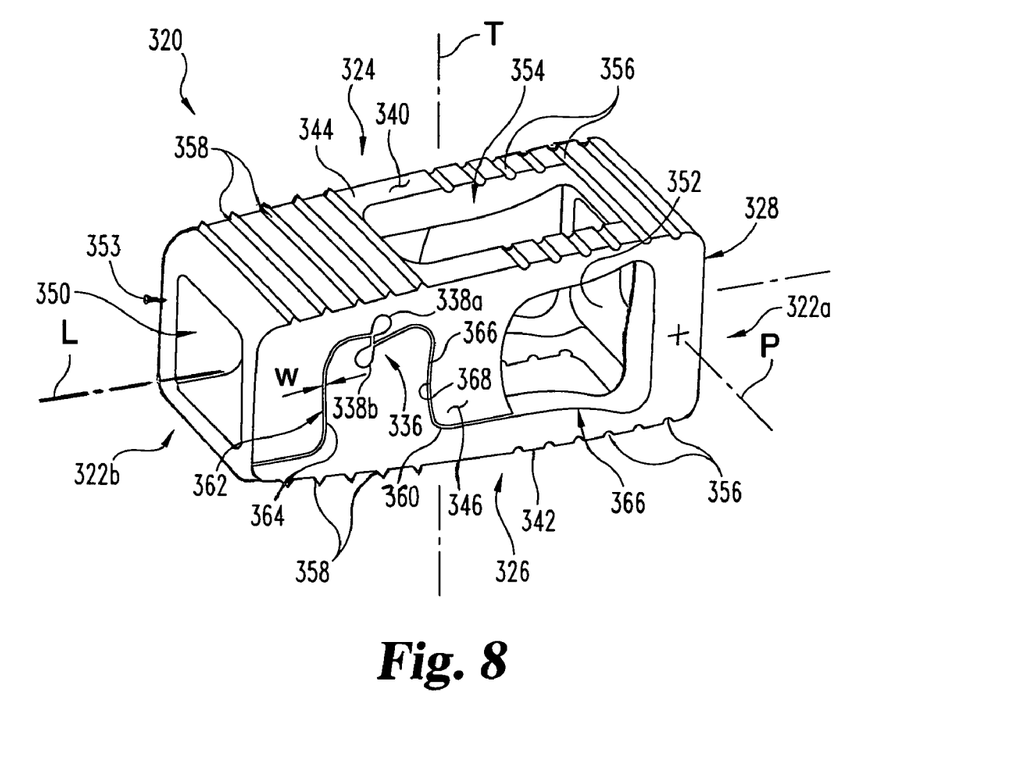
FIG. 8 is a side perspective view of an expandable spinal implant according to another form of the present invention.

Referring to FIG. 8, illustrated therein is an expandable spinal implant 320 according to another form of the present invention. The spinal implant 320 extends along a longitudinal axis L and is configured to expand generally along a transverse axis T so as to distract an intervertebral disc space and/or to restore or maintain lordosis between the adjacent vertebrae. However, it should be understood that expansion of the spinal implant 320 may occur in multiple directions and along multiple axes. In the illustrated embodiment, expansion of the spinal implant 320 results from relative pivotal movement of the branch portions 324, 326 about a pivot axis P positioned along the fixed base portion 328. However, other types of relative movement between the branch portions 324, 326 are also contemplated as falling within the scope of the present invention.

In one embodiment, expansion of the spinal implant 320 occurs in response to axial displacement of an expansion member (not shown) generally along the longitudinal axis L, which in turn separates the branch portions 324, 326 apart to expand the spinal implant 320 along the transverse axis T. Additionally, the spinal implant 320 includes a retention element or step feature 336 configured for engagement by the expansion member to secure the spinal implant in a select expanded configuration. In the illustrated embodiment, the retention element 336 comprises a pair of adjacent openings 338a, 338b extending through the upper and lower branch portions 324, 326 which are sized and shaped to receive corresponding portions of the expansion member therein. The expansion member is engaged and retained within each of the openings 338a, 338b and separates the upper and lower branch portions 324, 326 apart in an incremental manner so as to incrementally expand the spinal implant 320 along the transverse axis T.

In the illustrated embodiment, the branch portions 324, 326 define oppositely-disposed upper and lower bone engaging surfaces 340, 342 each having a generally flat or planar configuration, and oppositely-disposed side surfaces 344, 346 extending between the bone engaging surfaces 340, 342 and also having a generally flat or planar configuration. In one embodiment, the branch portions 324, 326 cooperate with one another to define a substantially rectangular outer cross section. However, it should be understood that other shapes and configurations of the spinal implant 320 and the branch portions 324, 326 are also contemplated as falling within the scope of the present invention.

In a further embodiment of the invention, the branch portions 324, 326 cooperate with one another to define a hollow interior or passage 350 extending generally along the longitudinal axis L. However, it should be understood that other embodiments of spinal implants are also contemplated that do not define a hollow interior, but instead define a substantially solid configuration. A bone growth promoting material may be positioned within the hollow interior 350 of the spinal implant 320 to facilitate fusion with the adjacent vertebrae. Additionally, an opening or passage 352 is defined through the fixed base portion 328 to provide access to the hollow interior 350 for loading the bone growth promoting material into the hollow interior 350 and/or for receiving an end portion of an instrument or tool therethrough and into engagement with the expansion member to transition the spinal implant 320 to the expanded configuration. The spinal implant 320 may also define an open distal end 353. Additionally, each of the branch portions 324, 326 defines at least one bone in-growth opening or window 354 extending through the bone engaging surfaces 340, 342 and communicating with the hollow interior 350 to permit bone growth from the adjacent vertebrae and into and possibly through the spinal implant 320.

In a further embodiment of the invention, the bone engaging surfaces 340, 342 may define a number of bone anchoring elements adapted for engagement with the adjacent vertebrae to prevent or inhibit movement of the spinal implant 320 once implanted within the intervertebral disc space. In the illustrated embodiment, the bone anchoring elements include a series of grooves 356 and a series of teeth 358. However, it should be understood that other types of bone anchoring elements are also contemplated including, for example, ridges, spikes, threads, surface roughening, or other suitable types and configurations of bone anchoring elements.

In order to facilitate expansion of the spinal implant 320 along the transverse axis T, the branches 324, 326 are separated from one another by a wire-like slot or channel 360 extending longitudinally from the distal end 322b toward the proximal end 322a and terminating adjacent the fixed base portion 328. The slot 360 extends laterally through the spinal implant 320 so as to divide the spinal implant 320 into two discrete upper and lower branch portions 324, 326. In the illustrated embodiment, the slot 360 terminate at an enlarged slot portion 366 adjacent the fixed base portion 328 to increase flexibility at the interconnection location between the branch portions 324, 326 and the fixed base portion 328 to facilitate transitioning of the spinal implant 320 to an expanded configuration, while at the same time tending to decrease stress concentrations which might otherwise develop at the interconnection location. Additionally, the enlarged slot portion 366 also provides additional passageways for bone in-growth into the hollow interior 350. The enlarged slot portion 366 may also be used as a means for receiving a corresponding portion of an instrument or tool to aid in the manipulation and handing of the spinal implant 320.

In the illustrated embodiment, the slot 360 includes a U-shaped portion that provides the branch portions 324, 326 with a projection 362 nested within a corresponding recess 364, with the projection 362 and the recess 364 extending generally along the transverse axis T. In one embodiment, the shape and configuration of the slot 360 provides the upper branch portion 324 with the recess 364 and the lower branch portion 326 with the projection 362, however, a reverse configuration is also contemplated. The projection 362 is nested within the recess 364 in a puzzle-like manner.

In one embodiment of the invention, the width w of the slots 360 is narrow to provide a relatively close or congruent fit between the axially-facing surfaces 366 of the projection 362 and the axially-facing surfaces 368 of the recess 364. In a further embodiment, the axially-facing surfaces 366, 368 each extend generally along a radial arc relative to the pivot axis P. In this manner, the opposing axially-facing surfaces 366, 368 will not interfere with one another as the upper and lower branches 324, 326 are separated or splayed apart during expansion of the spinal implant 320. Although a specific configuration of the slots 360 has been illustrated and described herein, it should be understood that other suitable slot configurations are also contemplated as falling within the scope of the present invention.

As should be appreciated, during expansion of the spinal implant 320, the projection 362 is radially displaced along the recess 364 relative to the pivot axis P. As the spinal implant 320 is transitioned to the expanded configuration, a portion of the projection 362 is maintained within the recess 364 in an interdigitating or interlocking manner to provide structural support to the expanded spinal implant 320. Engagement between the axially-facing surfaces 366 of the projection 362 and the axially-facing surfaces 368 of the recess 364 resists physiologic loading of the spinal implant 320 in the direction of the longitudinal axis L, and more particularly shear loading forces exerted onto the spinal implant by the adjacent vertebrae. Additionally, engagement of the projection 362 within the recess 364 resists buckling of the relatively thin fixed base portion 328 in response to the compressive loading forces exerted onto the spinal implant by the adjacent vertebrae. Moreover, the close congruity and interdigitating fit of the projection 362 within the recess 364 provide structural support to the spinal implant 320 which resists physiologic shear and bucking loading without significantly impeding or effecting the expansion characteristics of the spinal implant 320.

Figure 9:
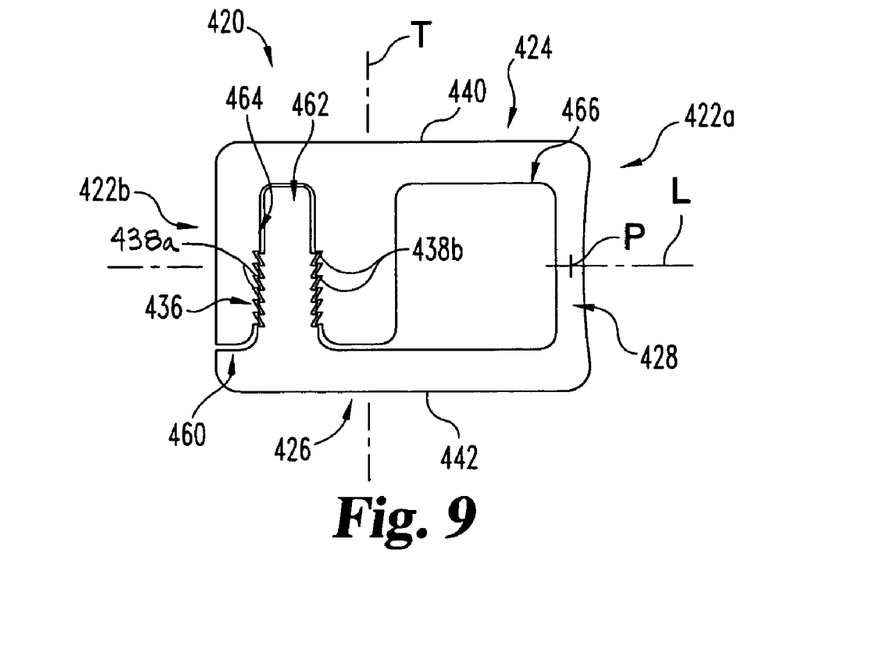
FIG. 9 is a side view of an expandable spinal implant according to another form of the present invention, as shown in a non-expanded state.
Figure 10:
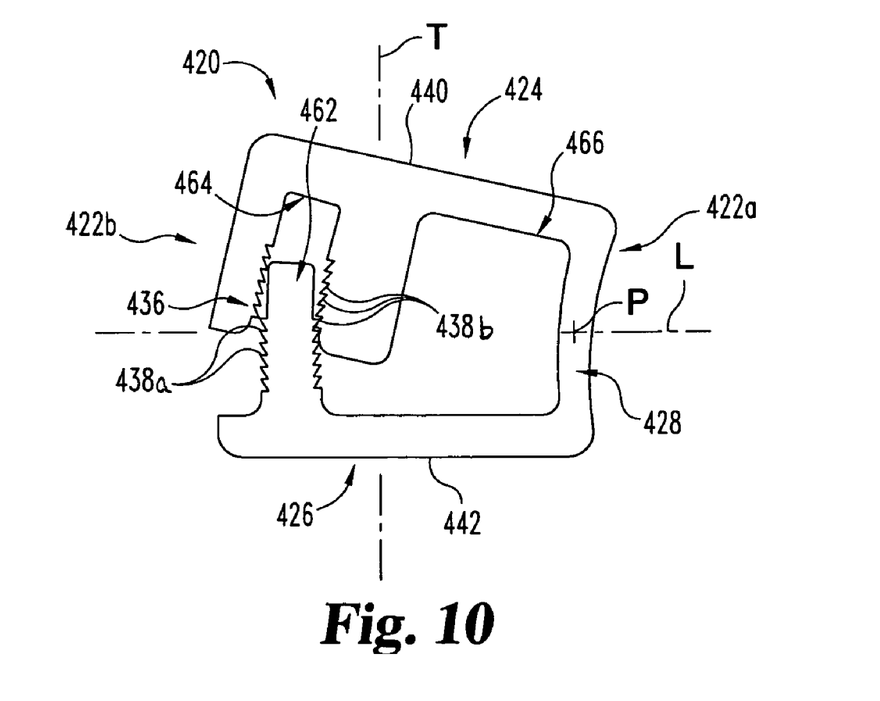
FIG. 10 is a side view of the expandable spinal implant illustrated in FIG. 9, as shown in an expanded state.

Referring to FIGS. 9 and 10, illustrated therein an expandable spinal implant 420 according to another form of the present invention. The illustrated embodiment of the spinal implant 420 extends along a longitudinal axis L and is in many respects structurally similar to the spinal implant 320 illustrated and described above, including upper and lower branch portions 424, 426 interconnected by a fixed base portion 428 in a manner allowing expansion of the spinal implant 420 generally along a transverse axis T. Additionally, in order to facilitate expansion of the spinal implant 420 along the transverse axis T, the branches 424, 426 are separated from one another by a wire-like slot or channel 460 extending longitudinally from the distal end 422b of the spinal implant 420 toward the proximal end 422a and terminating adjacent the fixed base portion 428. The slot 460 extends laterally through the spinal implant 420 so as to divide the spinal implant 420 into two discrete upper and lower branch portions 424, 426.

In the illustrated embodiment, the slot 460 terminates at an enlarged slot portion 466 adjacent the fixed base portion 428 to increase flexibility at the interconnection location between the branch portions 424, 426 and the fixed base portion 428 to facilitate transitioning of the spinal implant 420 to an expanded configuration, while at the same time tending to decrease stress concentrations which might otherwise develop at the interconnection location. The slot 460 includes also a U-shaped portion that provides the branch portions 424, 426 with a projection or post 462 nested within a corresponding recess or channel 464, with the projection 462 and the recess 464 extending generally along the transverse axis T. In one embodiment, the shape and configuration of the slot 460 provides the upper branch portion 424 with the recess 464 and the lower branch portion 426 with the projection 462, however, a reverse configuration is also contemplated.

The projection 462 is nested within the recess 464 in a puzzle-like manner. In the illustrated embodiment, the projection 462 and the recess 464 each define a number of retention elements 436 to maintain the spinal implant 420 in a select expanded configuration. In one embodiment, the retention elements 436 comprise a number of snap members or ratchets/pawls 438a defined transversely along the projection 462 and a number of snap members or ratchets/pawls 438b defined transversely along the recess 464. In a further embodiment, a plurality of the ratchets/pawls 438a, 438b are defined along each of the projection 462 and the recess 464. However, it should be understood that in other embodiments, either the projection 462 or the recess 464 may define a single ratchet/pawl 438a, 438b.

As should be appreciated, the ratchets/pawls 438a, 438b serve as retention elements or interlock features that retain or lock the spinal implant 420 in a select expanded configuration. As should also be appreciated, the ratchets/pawls 438a, 438b cooperate with one another to allow the upper and lower branch portions 424, 426 to be displaced apart during incremental expansion of the spinal implant 420, while at the same time preventing displacement of the upper and lower branch portions 424, 426 toward one another subsequent to expansion to thereby maintain the spinal implant 420 in a select expanded configuration. Although a specific embodiment of the retention elements 436 has been illustrated and described herein, it should be understood that other types and configurations of retention elements or interlock features suitable for maintaining the spinal implant 420 in a select expanded configuration are also contemplated.

Referring to FIG. 10, during expansion of the spinal implant 420, the projection 462 is displaced along the recess 464, with a portion of the projection 462 maintained within the recess 464 and with the ratchets/pawls 438a, 438b engaged in an interdigitating or interlocking manner to maintain the spinal implant 420 in a select expanded configuration and to provide structural support to the expanded spinal implant 420. Engagement of the projection 462 within the recess 464 also resists physiologic loading of the spinal implant 420 in the direction of the longitudinal axis L, and more particularly shear loading forces exerted onto the spinal implant by the adjacent vertebrae. Additionally, engagement of the projection 462 within the recess 464 resists buckling of the relatively thin fixed base portion 428 in response to the compressive loading forces exerted onto the spinal implant by the adjacent vertebrae. Moreover, the close congruity and interdigitating fit of the projection 462 within the recess 464 provides structural support to the spinal implant 420 which resists physiologic shear and bucking loading without significantly impeding or effecting the expansion characteristics of the spinal implant 420.

In one embodiment, a spreader or distractor-type instrument (not shown) having first and second end portions engaged with the upper and lower branch portions 424, 426, respectively, may be used to exert an outward force onto the branch portions 424, 426 to transition the implant 420 to an expanded configuration. However, other devices and techniques may be used to expand the spinal implant 420 such as, for example, via a wedge-type expansion member similar to the expansion member 30 illustrated and described above with regard to the spinal implant 20.

In one embodiment of the invention, access to the spinal column and insertion of the spinal implants into the intervertebral disc space is accomplished via a posterior surgical approach. However, it should be understood that access to and insertion of the spinal implants into the intervertebral disc space may be accomplished via other surgical approaches, such as, for example, an anterior approach or a lateral approach. In another embodiment of the invention, the spinal implants are used to treat the lumbar region of the spine. However, it should nevertheless be understood that the present invention is also applicable to other portions of the spine, including the cervical, thoracic or sacral regions of the spine. Additionally, in a further embodiment of the invention, a pair of spinal implants may be positioned side-by-side in a bilateral arrangement within the intervertebral disc space. However, it should be understood that unilateral placement or central placement of a single spinal implant embodiment within the intervertebral disc space is also contemplated as falling within the scope of the present invention.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An expandable spinal implant, comprising:
a body extending generally along a longitudinal axis between a first end portion and a second end portion, said body defining at least one slot extending generally along said longitudinal axis from said first end portion toward said second end portion to provide said body with at least two expandable branch portions coupled together adjacent said second end portion, said slot including a narrow portion defining close fitting interlocking features between said branch portions to provide structural support to the implant subsequent to expansion, wherein said narrow portion of said slot defines at least one transverse projection associated with a first of said branch portions and at least one transverse recess associated with a second of said branch portions and defining opposing axially-facing inner surfaces that oppose one another along said longitudinal axis, said transverse projection positioned within and displacable along said transverse recess and engaged with said opposing axially-facing inner surfaces subsequent to said expansion of the implant and separation of said at least two expandable branch portions away from one another to provide said structural support to the expanded implant by said close fitting interlocking features between said branch portions; and
an interlocking retention element interlocked between said at least two branch portions adjacent said first end portion to prevent movement of said branch portions toward one another to maintain said body in a select expanded configuration.

2. The implant of claim 1, wherein said transverse projection defines opposite axially-facing outer surfaces, said opposing axially-facing inner surfaces of said transverse recess arranged generally parallel with one another, said outer surfaces of said transverse projection positioned in close proximity with respective ones of said inner surfaces of said transverse recess to provide said structural support to the implant subsequent to expansion.

3. The implant of claim 1, wherein said branch portions are pivotally displaced relative to one another about a pivot axis during expansion of the implant, said transverse projection and said transverse recess defining an adjacent pair of surfaces having a similar radius of curvature relative to said pivot axis.

4. The implant of claim 1, wherein said branch portions are coupled together adjacent said second end portion of said body to allow relative pivotal movement therebetween about a pivot axis, said transverse projection extending generally along a radial arc relative to said pivot axis, said transverse recess also extending generally along said radial arc.

5. The implant of claim 1, wherein said branch portions are coupled together adjacent said second end portion of said body to allow relative pivotal movement therebetween about said pivot axis, said transverse projection having an arcuate outer surface extending generally along a radial arc relative to said pivot axis, said transverse recess having an arcuate inner surface extending generally along said radial arc, said arcuate outer surface of said transverse projection positioned in close proximity with said arcuate inner surface of said transverse recess to provide said structural support to the implant subsequent to expansion.

6. The implant of claim 1, wherein said first of said branch portions includes a first bone engaging surface adapted to engage an adjacent vertebra and with said projection arranged transverse to said first bone engaging surface, said second of said branch portions including a second bone engaging surface adapted to engage an adjacent vertebra and with said recess arranged transverse to said second bone engaging surface.

7. The implant of claim 6, wherein said first and second bone engaging surfaces are arranged parallel to one another when the implant is in a non-expanded insertion configuration.

8. The implant of claim 6, wherein said first and second bone engaging surfaces are tapered relative to one another when the implant is in a non-expanded insertion configuration.

9. The implant of claim 1, wherein said transverse projection and said transverse recess define a number of said interlocking retention elements configured to maintain the implant in said select expanded configuration.

10. The implant of claim 9, wherein said interlocking retention elements comprise interlocking ratchet elements.

11. The implant of claim 1, wherein said second end portion of said body has an outer surface facing away from said branch portions and defining a concave curvature to facilitate transverse expansion of the implant.

12. The implant of claim 1, wherein said slot includes an enlarged portion adjacent said second end of said body to facilitate transverse expansion of the implant.

13. The implant of claim 1, wherein said narrow portion of said slot has an undulating configuration.

14. The implant of claim 1, wherein said narrow portion of said slot has a curved configuration.

15. The implant of claim 1, wherein said branch portions are formed integral with said second end portion of said body to define a single-piece unitary implant body.

16. The implant of claim 1, wherein at least a portion of the implant is formed of a shape-memory material to provide the implant with a self-expanding capability.

17. The implant of claim 1, wherein said branch portions cooperate to define an inner passage sized to receive an expansion member therein; and wherein displacement of said expansion member within said inner passage engages said expansion member with said branch portions to expand the implant.

18. The implant of claim 17, wherein said displacement comprises movement of said expansion member within said inner passage generally along said longitudinal axis.

19. The implant of claim 17, wherein said branch portions have inner surfaces defining said inner passage, said inner surfaces cooperating to define a taper along said longitudinal axis, said expansion member engaging said inner surfaces to displace said branch portions away from one another as said expansion member is displaced generally along said longitudinal axis.

20. The implant of claim 17, wherein at least one of said branch portions includes a notch adapted to engage and retain said expansion member in a select position upon expansion of the implant, said notch and said expansion member cooperating to provide said interlocking retention element.

21. The implant of claim 20, wherein said branch portions include a pair of opposing ones of said notch sized and shaped to receive a portion of said expansion member therein.

22. The implant of claim 1, wherein said at least two expandable branch portions cooperate to define a hollow interior of said body; and further comprising a bone growth promoting substance disposed within said hollow interior to facilitate fusion with adjacent vertebrae.

23. The implant of claim 22, wherein said bone growth promoting substance comprises a bone morphogenic protein.

24. An expandable spinal implant, comprising:

at least two expandable branch portions extending generally along a longitudinal axis, each of said branch portions including a fixed end portion and an opposite movable end portion with each of said fixed end portions coupled together adjacent a fixed base portion of the implant, a first of said branch portions including at least one transverse projection having opposite axially-facing outer surfaces, a second of said branch portions defining at least one transverse recess having opposing axially-facing inner surfaces that oppose one another along said longitudinal axis, said projection positioned within and displacable along said recess with said outer surfaces of said projection positioned in close proximity with respective ones of said inner surfaces of said recess to provide structural support to the implant subsequent to expansion of the implant and separation of said at least two expandable branch portions away from one another; and an interlocking retention element interlocked between said at least two branch portions adjacent said movable end portion to prevent movement of said branch portions toward one another to maintain said body in a select expanded configuration.

25. The implant of claim 24, wherein said branch portions are separated from one another by at least one slot, said at least one slot including a narrow portion defining said transverse projection associated with said first of said branch portions and defining said transverse recess associated with said second of said branch portions.

26. The implant of claim 24, wherein said branch portions are coupled together adjacent said fixed base portion in a manner that allows relative pivotal movement therebetween about a pivot axis, said transverse projection extending generally along a radial arc relative to said pivot axis, said transverse recess also extending generally along said radial arc.

27. The implant of claim 24, wherein said first of said branch portions includes a first bone engaging surface adapted to engage an adjacent vertebra and with said projection arranged transverse to said first bone engaging surface, said second of said branch portions including a second bone engaging surface adapted to engage an adjacent vertebra and with said recess arranged transverse to said second bone engaging surface.

28. The implant of claim 24, wherein said fixed base portion has an outer surface facing away from said branch portions and defining a concave curvature to facilitate transverse expansion of the implant.

29. The implant of claim 24, wherein said transverse projection and said transverse recess define a number of said interlocking retention elements configured to maintain the implant in said select expanded configuration.

30. The implant of claim 29, wherein said interlocking retention elements comprise interlocking ratchet elements.

31. The implant of claim 24, wherein said at least two expandable branch portions cooperate to define a hollow interior; and
further comprising a bone growth promoting substance disposed within said hollow interior to facilitate fusion with adjacent vertebrae.

32. The implant of claim 31, wherein said bone growth promoting substance comprises a bone morphogenic protein.

33. The implant of claim 24, wherein said branch portions are formed integral with said fixed base portion to define a single-piece unitary implant body.

34. The implant of claim 24, wherein at least a portion of the implant is formed of a shape-memory material to provide the implant with a self-expanding capability.

35. The implant of claim 24, wherein said branch portions cooperate to define an inner passage sized to receive an expansion member therein; and
wherein displacement of said expansion member within said inner passage engages said expansion member with said branch portions to expand the implant.

36. The implant of claim 24, wherein said transverse projection is formed integral with said first of said branch portion to define a single-piece unitary structure.

37. An expandable spinal implant, comprising:
at least two expandable branch portions extending generally along a longitudinal axis, each of said branch portions including a fixed end portion and an opposite movable end portion with each of said fixed end portions coupled together adjacent a fixed base portion of the implant, a first of said branch portions including a first bone engaging surface adapted to engage an adjacent vertebra and defining at least one projection arranged transverse to said first bone engaging surface, a second of said branch portions including a second bone engaging surface adapted to engage an adjacent vertebra and defining at least one recess arranged transverse to said second bone engaging surface and defining opposing axially-facing inner surfaces that oppose one another along said longitudinal axis, said projection positioned within and displacable along said recess and engaged with said opposing axially-facing inner surfaces to provide structural support to the implant subsequent to expansion of the implant and separation of said at least two expandable branch portions away from one another; and
an interlocking retention element interlocked between said at least two branch portions adjacent said movable end portion to prevent movement of said branch portions toward one another to maintain said body in a select expanded configuration.

38. The implant of claim 37, wherein said branch portions are separated from one another by at least one slot, said at least one slot including a narrow portion defining said projection associated with said first of said branch portions and defining said recess associated with said second of said branch portions.

39. The implant of claim 37, wherein said projection defines opposite axially-facing outer surfaces, said opposing axially-facing inner surfaces of said recess arranged generally parallel with one another, said outer surfaces of said projection positioned in close proximity with respective ones of said inner surfaces of said recess to provide said structural support to the implant subsequent to expansion.

40. The implant of claim 39, wherein said branch portions are pivotally displaced relative to one another about a pivot axis during expansion of the implant, each of said axially-facing outer surfaces of said projection having a radius of curvature relative to said pivot axis, each of said axially-facing inner surfaces of said recess having a radius of curvature relative to said pivot axis, said radius of curvature of said outer surfaces corresponding to said radius of curvature of adjacent ones of said inner surfaces.

41. The implant of claim 37, wherein said branch portions are pivotally displaced relative to one another about a pivot axis during expansion of the implant, said projection extending generally along a radius of curvature relative to said pivot axis, said recess also extending generally along said radius of curvature.

42. The implant of claim 37, wherein said fixed base portion has an outer surface facing away from said branch portions and defining a concave curvature to facilitate transverse expansion of the implant.

43. The implant of claim 37, wherein said projection and said recess define a number of said interlocking retention elements configured to maintain the implant in said select expanded configuration.

44. The implant of claim 4, wherein said interlocking retention elements comprise interlocking ratchet elements.

45. The implant of claim 17, wherein said branch portions are formed integral with said fixed base portion to define a single-piece unitary implant body.

46. The implant of claim 17, wherein said projection is formed integral with said first of said branch portion to define a single-piece unitary structure.

47. An expandable spinal implant, comprising:
at least two expandable branch portions extending generally along a longitudinal axis, said branch portions coupled together to allow relative pivotal movement therebetween about a pivot axis, a first of said branch portions including at least one projection that defines opposite axially-facing arcuate outer surfaces extending generally along a radial arc relative to said pivot axis, a second of said branch portions defining at least one recess, said recess defining opposing axially-facing arcuate inner surfaces extending generally along said radial arc, said projection positioned within and displacable along said recess, said arcuate outer surfaces of said projection positioned in close proximity with respective ones of said arcuate inner surfaces of said recess to provide structural support to the implant subsequent to expansion and separation of said at least two expandable branch portions away from one another; and
wherein each of said branch portions includes a fixed end portion and an opposite movable end portion with each of said fixed end portions coupled together at a fixed base portion of the implant to allow said relative pivotal movement about said pivot axis; and wherein said branch portions are formed integral with said fixed base portion to define a single-piece unitary implant body.

48. An expandable spinal implant, comprising:

at least two expandable branch portions extending generally along a longitudinal axis, said branch portions coupled together to allow relative pivotal movement therebetween about a pivot axis, a first of said branch portions including at least one projection that defines opposite axially-facing arcuate outer surfaces extending generally along a radial arc relative to said pivot axis, a second of said branch portions defining at least one recess, said recess defining opposing axially-facing arcuate inner surfaces extending generally along said radial arc, said projection positioned within and displacable along said recess, said arcuate outer surfaces of said projection positioned in close proximity with respective ones of said arcuate inner surfaces of said recess to provide structural support to the implant subsequent to expansion and separation of said at least two expandable branch portions away from one another; and wherein each of said branch portions includes a fixed end portion and an opposite movable end portion with each of said fixed end portions coupled together at a fixed base portion of the implant to allow said relative pivotal movement about said pivot axis; and wherein said fixed base portion has an outer surface facing away from said branch portions and defining a concave curvature to facilitate said relative pivotal movement about said pivot axis.

49. An expandable spinal implant, comprising:

at least two expandable branch portions extending generally along a longitudinal axis, said branch portions coupled together to allow relative pivotal movement therebetween about a pivot axis, a first of said branch portions including at least one projection that defines opposite axially-facing arcuate outer surfaces extending generally along a radial arc relative to said pivot axis, a second of said branch portions defining at least one recess, said recess defining opposing axially-facing arcuate inner surfaces extending generally along said radial arc, said projection positioned within and displacable along said recess, said arcuate outer surfaces of said projection positioned in close proximity with respective ones of said arcuate inner surfaces of said recess to provide structural support to the implant subsequent to expansion and separation of said at least two expandable branch portions away from one another.

50. The implant of claim 49, wherein each of said branch portions includes a fixed end portion and an opposite movable end portion with each of said fixed end portions coupled together at a fixed base portion of the implant to allow said relative pivotal movement about said pivot axis.

51. The implant of claim 49, wherein said branch portions are separated from one another by at least one slot, said at least one slot including a narrow portion defining said projection associated with said first of said branch portions and defining said recess associated with said second of said branch portions.

52. The implant of claim 49, wherein said projection is formed integral with said first of said branch portions to define a single-piece unitary structure.

53. The implant of claim 50, wherein said pivot axis extends through said fixed base portion.

54. The implant of claim 49, wherein said opposing axially-facing inner surfaces of said recess are arranged generally parallel with one another and are offset from one another along the longitudinal axis.

55. The implant of claim 49, wherein said at least one projection is radially displaced along a length of said at least one recess and generally along said radial arc during expansion and separation of said at least two expandable branch portions away from one another.

* * * * *